United States Patent [19]
Campbell

[11] Patent Number: 5,762,612
[45] Date of Patent: Jun. 9, 1998

[54] MULTIMODAL STIMULATION IN VIRTUAL ENVIRONMENTS

[76] Inventor: Craig Campbell, 27 Bailey Ave., Pittsburgh, Pa. 15211

[21] Appl. No.: 810,611

[22] Filed: Feb. 28, 1997

[51] Int. Cl.⁶ ..................................................... A61B 5/00
[52] U.S. Cl. ........................... 600/558; 600/559; 600/595
[58] Field of Search ..................................... 600/558, 559, 600/587, 595; 607/55, 56, 136, 137

[56] References Cited

U.S. PATENT DOCUMENTS

| | | |
|---|---|---|
| 5,347,400 | 9/1994 | Hunter . |
| 5,394,517 | 2/1995 | Kalawsky . |
| 5,459,382 | 10/1995 | Jacobus et al. . |
| 5,482,051 | 1/1996 | Reddy et al. . |
| 5,490,239 | 2/1996 | Myers . |
| 5,490,784 | 2/1996 | Carmein . |

*Primary Examiner*—Max Hindenburg
*Attorney, Agent, or Firm*—Kenneth P. McKay, Esq.

[57] ABSTRACT

Galvanic vestibular stimulation is combined with visual stimulation to extend movement and directional cues within a virtual reality scene. The vestibular sensory system will be stimulated through the use of galvanic stimulation to induce a state of vestibular dysequilibrium. Synchronizing this inner-ear dysequilibrium with an optical reference will amplify the user's postural movement. The current state of virtual reality stimulates principally only the visual scene of the user through head mounted visual display units. However, the human body uses three different senses to resolve motion and acceleration cues like those simulated in virtual reality. Reliance on the visual scene, therefore, necessarily invites conflict between the visual system and the two remaining centers for motion sensation which remain dormant and, therefore, do not reinforce the visual sensations. This confuses the user and detracts from the experience. The instant invention negates this distraction through the use of galvanic stimulation of the user's vestibular system utilized in conjunction with the visual stimulation within virtual reality environments.

10 Claims, 3 Drawing Sheets

MULTIMODAL STIMULATION IN VIRTUAL ENVIRONMENTS

BACKGROUND OF THE INVENTION

1. Field of the Invention

The present invention relates generally to the coupling of visual and vestibular stimuli to extend movement and directional cues within a virtual reality scene.

2. Description of the Related Art

Today's virtual reality systems provide visual stimulation for the user usually by means of a helmet mounted display apparatus comprising a pair of miniature visual display units arranged to project their images into respective user's eyes such that the image displayed is perceived stereoscopically, thereby creating the illusion that the image is three dimensional. These systems allow the user to interact with the displayed image by providing a means of monitoring movement of the user's head, and in some instances, movement of his eyes and other parts of the user's body. The feed-back information obtained by carefully monitoring these movements allows the system to generate and present different images to the user corresponding to changes in the user's line of sight.

The current state of virtual reality is limited by stimulation of principally only the visual scene through the visual display units. However, the human body uses three different senses to resolve motion and acceleration cues like those simulated in virtual reality. Visual stimulation is adequate to perceive the motion of an external object such as a bouncing ball, yet it is entirely insufficient to clearly interpret self-motion. Reliance on the visual scene, therefore, necessarily invites conflict between the visual system and the two remaining centers for motion sensation which remain dormant and, therefore, do not reinforce the visual sensations. This confuses the user and detracts from the experience.

The only current solution is a hydraulic motion platform or other mechanical device designed to replicate movement and acceleration cues. These devices involve a tremendous amount of space, capital investment and maintenance. Furthermore, these mechanisms are marginally adequate, at best, in replicating the given cues corresponding to the visual scene. The instant invention constitutes a more affordable and more effective alternative.

The instant invention represents a paradigm shift in the art of virtual reality. The use of galvanic stimulation of the vestibular system designed to correspond with the visual scene of a Virtual Reality environment is a concept that has never been proposed. Vestibular stimulation provides the movement and acceleration cues required to enhance virtual reality without the use of bulky and expensive mechanical devices.

Until now, galvanic stimulation of the vestibular system has only been utilized for the purpose of medical treatment and/or diagnosis of balance disorders. The instant invention expands the diagnostic uses of galvanic stimulation of the vestibular system in order to create a relationship between visual and vestibular cues in virtual reality.

The inner ear vestibular system is composed of two laterally symmetric sets of end organs. Each ear contains fine spatially specific end organs for sensing head accelerations. In each ear three semicircular canals sense angular accelerations in three approximately orthogonal axes. The utricular otoliths sense the sum of gravity and linear head accelerations in a plane inclined approximately 30 degrees from horizontal. Function of the saccule is less understood but is believed to include gravity and linear acceleration along an approximately vertical axis. Thus, individual vestibular end organs are involved in maintaining different components of posture and equilibrium. The horizontal canals are used primarily to control horizontal plane eye and head movements, while the vertical canals and otoliths help maintain front-to-back and side-to-side balance of the head and trunk. The spatial and functional specificity within the vestibular system provides an opportunity for selectively determining the extent of pathology of individual end organs by observing both head, eye, and body responses to vestibular stimulation. Galvanic vestibular stimulation involves the exciting of the end organs of one ear electrically by passing small currents between two or more surface electrodes affixed to the mastoid bone of the ear or other locations on the head. Various attempts have been made to use galvanic vestibular stimuli as a clinical diagnostic tool. Vestibular end organs can be selectively stimulated by passing small electrical currents between electrodes placed in different configurations on the mastoid bones. Placing one electrode on each mastoid bone stimulates receptors in both inner ears in opposite directions, while two electrodes placed on a single mastoid bone stimulate receptors of one ear selectively. Electrical stimulation of the vestibular receptor organs is a useful clinical diagnostic method, because it can be used to quantify receptor function of one ear at a time and because the time course and frequency of stimulation can be precisely controlled.

PRIOR ART

U.S. Pat. No. #5,347,400 (HUNTER), discloses an optical system for a virtual reality head mounted display.

U.S. Pat. No. #5,394,517 (KALAWSKY), discloses a display system that enables the effective integration of computer generated images with real, naturally occurring images in helmet mounted visual display units which provide the user with his or her entire visual stimulation.

U.S. Pat. No. #5,459,382 (JACOBUS ET AL.), discloses a system and method for implementing a tactile virtual reality environment in which the position and orientation of the user is utilized to generate a virtual reality force field.

U.S. Pat. No. #5,482,051 (REDDY ET AL.), discloses a system through which the user "squeezes" virtual objects, sees the object deform, and feels the deformation through the detection of an electromyographic signal from the musculature of the user.

U.S. Pat. No. #5,490,239 (MEYERS), discloses a virtual reality imaging system that creates a visual image of a multidimensional space to present a filtered image of various three dimensional phenomena and features that are contained within the multidimensional space as viewed from any predefined locus within the space.

U.S. Pat. No. #5,490,784 (CARMEIN), discloses a mechanical system for creating motion with six full degrees of freedom, three rotational and three linear-translational, in an attempt to electronically coordinate and reproduce sights, sounds and physical sensations in a capsule such that a user may interactively control and respond to a variety of environments while simultaneously experiencing the corresponding motion and physical sensations associated with the interactive environment.

U.S. Pat. No. #5,303,715 (NASHNER), discloses the testing of the presence of vestibular pathology in an embodiment wherein a subject has a control external stimulus, such as an electrical, caloric or barometric stimulus, applied to one or both inner ears.

SUMMARY OF THE INVENTION

The objective of the present invention is to achieve greater depth of sensation within virtual environments. In particular, this invention couples visual and vestibular stimuli to extend movement and directional cues within a virtual reality scene.

The vestibular sensory system will be stimulated through the use of galvanic stimulation to induce a state of vestibular dysequilibrium. Electrode pairs placed on the mastoid bone behind each ear and on the forehead provide the stimulation to the vestibular system. Synchronizing this inner-ear dysequilibrium with an optical reference will amplify the user's postural movement. The effect requires specific multimodal information to flow from the virtual environment to the subject in accord with our perceptions of behavior in the natural world. This can be accomplished by programming the galvanic stimulus to fire coactively with the visual scene. By isolating the pair, visual and vestibular, postural sway, reaction times and tracking dexterity improve. The current invention proffers that synthetic vestibular cues add fidelity to virtual reality simulations. Furthermore, engaging otherwise dormant loci of sensation will intensify the realism of a virtual reality experience.

DETAILED DESCRIPTION OF THE PREFERRED EMBODIMENT

The invention will now be described in detail in relation to a preferred embodiment and implementation thereof which is exemplary in nature and descriptively specific as disclosed. As is customary, it will be understood that no limitation of the scope of the invention is thereby intended, and that the invention encompasses such alterations and further modifications in the illustrated device, and such further applications of the principles of the invention illustrated herein, as would normally occur to persons skilled in the art to which the invention relates.

Figure 1:
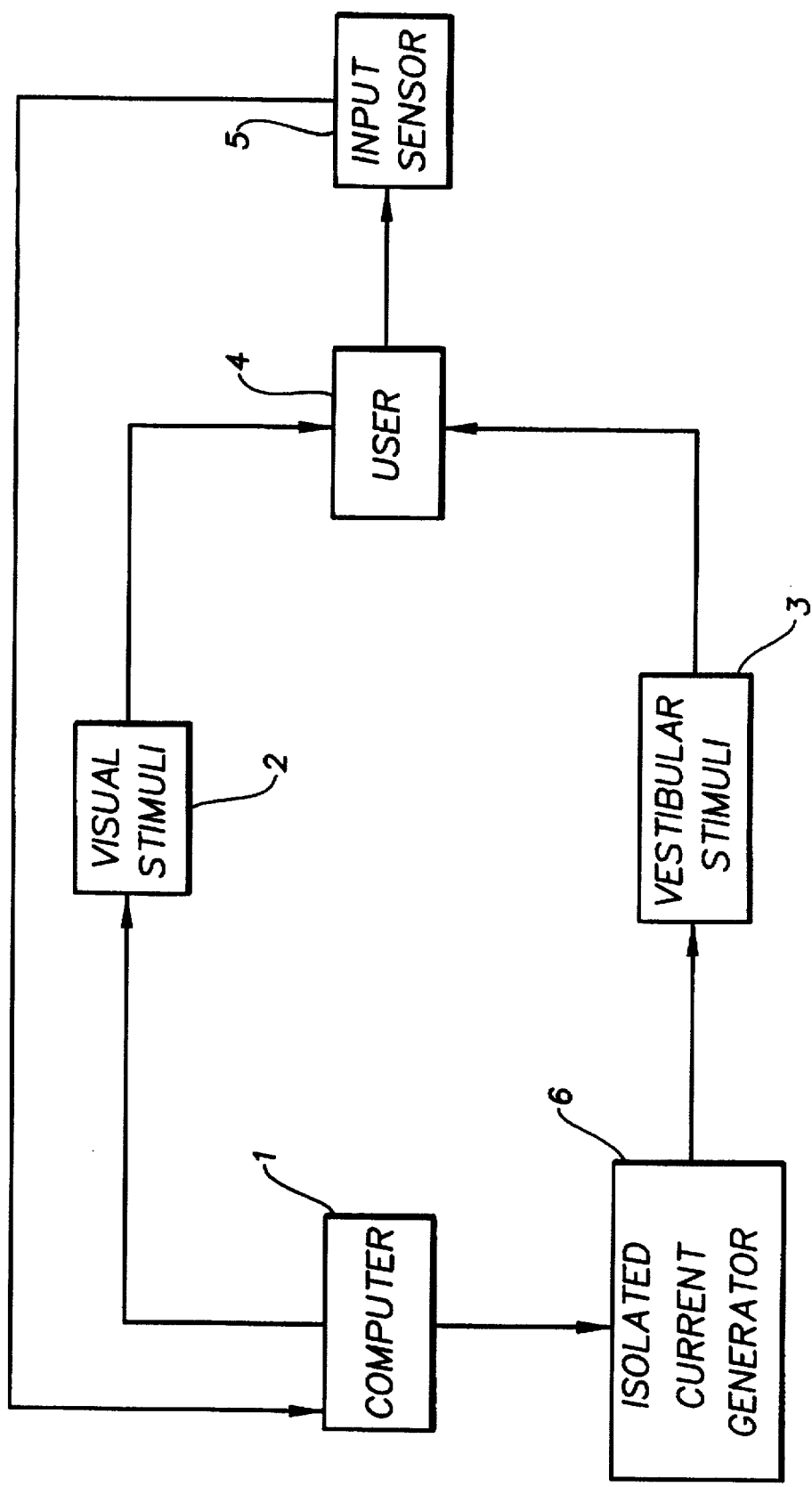
FIG. 1 is a block diagram showing a multimodal stimulation process within a virtual environment constructed in accordance with the present invention.

Thus, with reference now to FIG. 1, there is a block diagram showing a multimodal stimulation process within a virtual environment. A computer 1 running stimulation software, that can attach behaviors to objects and signal events with serial I/O, triggers both visual 2 and vestibular 3 stimulation from within a virtual reality environment as programmed. The software creates the visual stimulation 2 by projecting a visual scene onto a head mounted display unit 15 (See FIG. 3) worn by the user 4. Correspondingly, the stimulation software triggers the vestibular stimulation 3 by outputting a signal to the isolated current generator 6 which sends the appropriate galvanic stimulation to the galvanic electrodes 14 on the user's 4 head. Some type of input sensor 5, with between 2 and 6 degrees of freedom, tracks the user's 4 motion instantaneously returning the data to the stimulation software program.

Figure 2:
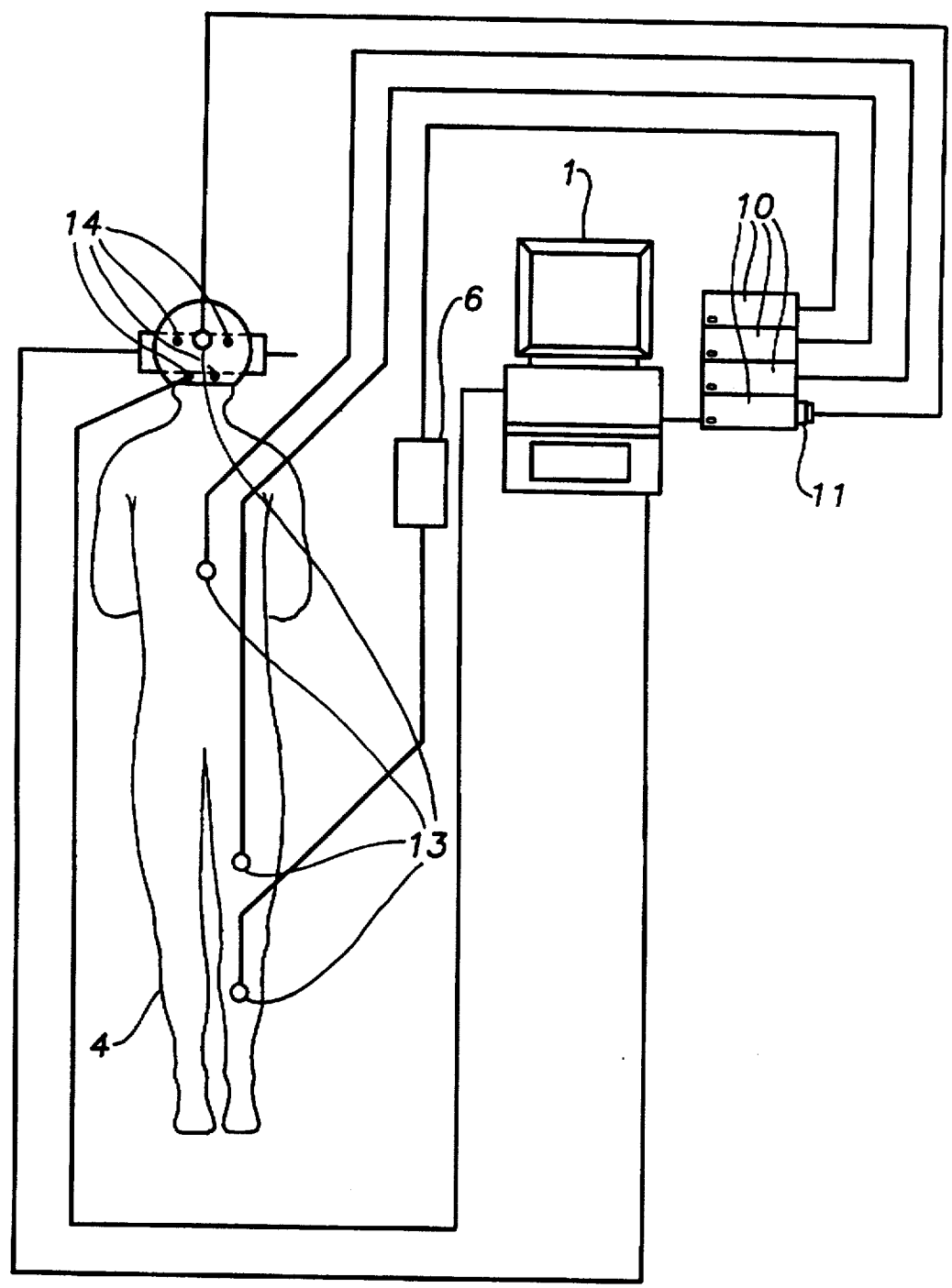
FIG. 2 is a diagrammatic illustration of a preferred embodiment of the entire scope of the current invention; and, FIG. 3 is a diagrammatic illustration of the interface between the head mounted display unit, the galvanic electrodes and the user.

Thus, with reference now to FIG. 2, there is illustrated a preferred embodiment of the scope of the current invention. The head mounted display unit 15 (See FIG. 3) is connected to the video port of the computer 1. The computer's 1 stimulation software transmits to the head mounted display unit 15 the video that provides the visual stimulation 2 to the user 4.

The user 4 has galvanic electrodes 14 attached to the user's 4 head. These galvanic electrodes 14 are connected to an isolated current generator 6. Corresponding to the visual stimulation 2 being received by the user 4, the stimulation software program running on the computer 1 sends the isolated current generator 6 a signal to trigger the galvanic electrodes 14 on the user 4 thereby providing the user 4 simultaneous and corresponding visual 2 and vestibular 3 stimuli.

Of course, the signal to trigger the galvanic electrodes 14 may be generated by a variety of devices and means, and in the preferred embodiment the device is an isolated current generator 6. The output from the isolated current generator 6 is variable in current magnitude and bandwidth. It has been found, however, that the optimum signal to trigger the galvanic electrodes 14 approximates a direct current of plus or minus one milliampere at an approximate band width of 2 Hz. The signal to trigger the galvanic electrodes 14 is adjustable such that it may be variably altered to allow for the variable stimulation of a variety of user 4 since persons have a varying impedance in their vestibular systems and variable resistances may be experienced among a variety of user 4.

All of the user's 4 movements are tracked and recorded by a three dimensional motion detection system 10 capable of recording both range and speed of motion with six degrees of freedom within an electromagnetic field. The three dimensional motion detection system 10 records kinematic data. An electromagnetic field is created around the user 4 by the electromagnetic field generator 11. The user's 4 movements are then detected by the program via magnetic transmitters 13 attached to the user 4 at one or more locations on the user's 4 body sufficient to detect the user's 4 movement dynamics. The data collected by the three dimensional motion detection system 10 is continuously sent to the stimulation software running on the computer 1.

Figure 3:
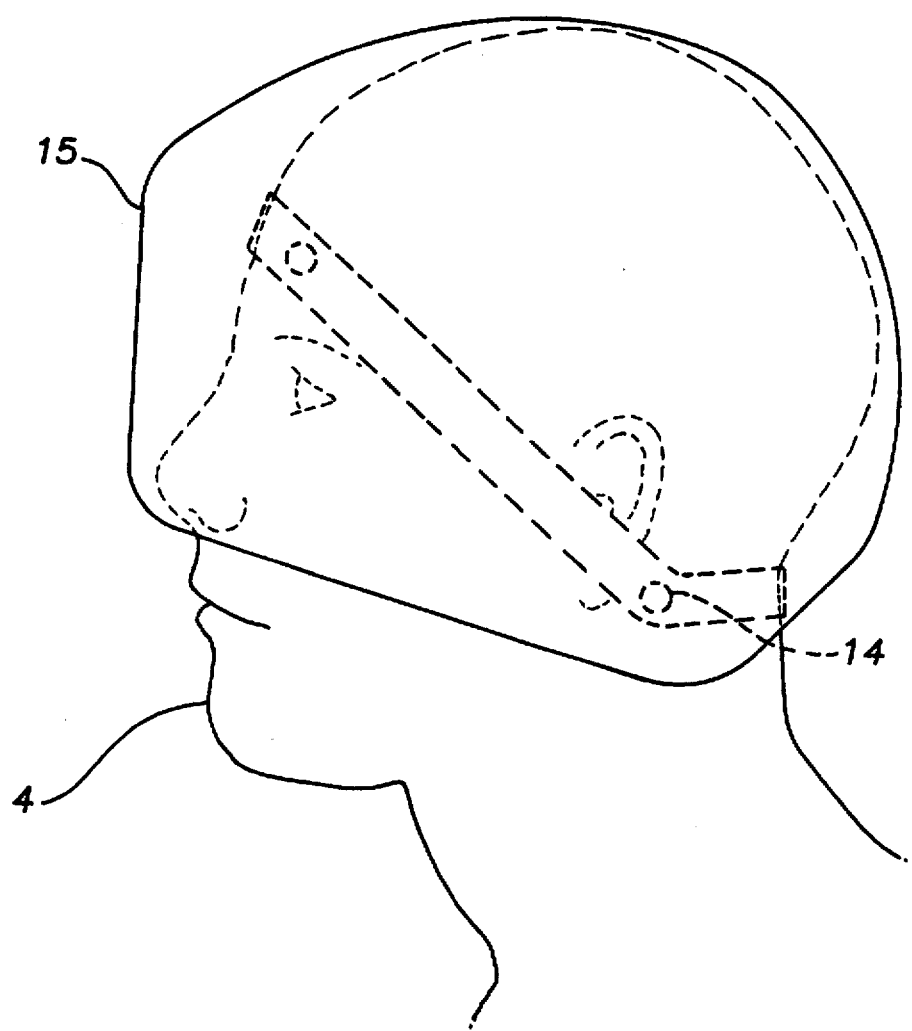

Thus, with reference now to FIG. 3, there is illustrated a graphic representation of the interface between the head mounted display unit 15 that will display the visual stimulation 2, the galvanic electrodes 14 and the user 1. The head mounted display unit 15 is placed on the user's 4 head after the galvanic electrodes 14 have been secured to the user 4. The galvanic electrodes 14 are attached at discrete locations on said user, particularly on or near the mastoid bone behind each ear and on the temples of the user 4. The user 4 may be thereby stimulated in directions both rotational about the user's 4 line of sight and perpendicular to the user's 4 line of sight.

I claim:

1. A process for inducing multimodal stimulation of a user within virtual environments, comprising:
   a. running a simulation software program on a computer, said simulation program having a plurality of output parameters;
   b. transmitting an output of the simulation software program to said user in the form of a visual scene;
   c. projecting said visual scene on a visual display mechanism being utilized by said user whereby said user is visually stimulated;
   d. providing another output of said software program to said user in the form of a signal to said user's vestibular system generated concurrently with said visual scene;

e. applying said signal to said user's vestibular system by means of galvanic electrodes attached to said user whereby said user is vestibularly stimulated;

f. taking motion input from said user as said user reacts to said vestibular stimulation and said visual stimulation;

g. converting said motion input from said user to data for transmission to said computer;

h. providing feedback of said data to the simulation software program;

i. coupling said feedback of said data to said simulation software program whereby said multitude of output parameters are altered in response to said motion input, and, j. repeating said process at high frequency whereby said user is continuously stimulated in a multimodal manner.

2. A process for inducing multimodal stimulation of a user within virtual environments, as claimed in claim 1, wherein said a signal to said user's vestibular system approximates a direct current of plus or minus one milliampere at an approximate band width of 2 Hz, and said signal is adjustable such that said signal may be altered in magnitude and band width to allow for the variable stimulation of said user.

3. A process for inducing multimodal stimulation of a user within virtual environments, as claimed in claim 1, wherein said signal to said user's vestibular system is applied by a plurality of galvanic electrodes, attached to said user at a location proximate to said user's mastoid bone at each ear.

4. A process for inducing multimodal stimulation of a user within virtual environments, as claimed in claim 1, wherein said signal to said user's vestibular system is applied by a plurality of galvanic electrodes, respectively attached to said user at a location proximate to said user's mastoid bone at each ear and a plurality of galvanic electrodes, respectively attached to said user at a location proximate to said user's forehead above each eye.

5. An apparatus for inducing multimodal stimulation of a user within virtual environments, comprising:

a. a computer;

b. a software program which is run by said computer and having as input from said computer a plurality of parameters which variably influence said computer program, said software program having the capability to provide an output signal from said computer for vestibular stimulation and an output signal from said computer for visual stimulation, and having the capability to coordinate said output signals in concert with each other;

c. a visual stimulation device visible to said user, said visual stimulation device being coupled with said output signal from said computer for visual stimulation, whereby a visual scene is formed upon said visual stimulation device;

d. an isolated current generator having as input said output signal from said computer for vestibular stimulation and having as output a direct current;

e. a vestibular stimulation device connected to said isolated current generator, said vestibular stimulation device being responsive to said direct current, whereby said user is vestibularly stimulated by said vestibular stimulation device concurrent with said visual scene, and whereby said user relates to said vestibular stimulation in concert with said visual scene by response in the form of physical movement;

f. a three dimensional motion detection system having as input said physical movement by said user and capable of response to said input in the form of signals, whereby said three dimensional motion detection system provides an output signal in response to physical movement by said user which is translated to feedback data;

g. a feedback loop such that said feedback data is transmitted to said computer as an input to said computer and whereby said computer provides said feedback data into said software program as a parameter which variably influences said computer program, and whereby said output signal from said computer for vestibular stimulation and said output signal from said computer for visual stimulation are adjusted in response to said physical movement of said user, thereby repetitively inducing multimodal stimulation of said user.

6. An apparatus as claimed in claim 5, wherein said visual stimulation device further comprises a head mounted display worn by said user.

7. An apparatus as claimed in claim 5, wherein said vestibular stimulation device further comprises a plurality of galvanic electrodes attached to said user, a minimum of at least one said galvanic electrode being attached to said user in an area proximate to the mastoid bone behind each ear.

8. An apparatus as claimed in claim 5, wherein said vestibular stimulation device further comprises a plurality of galvanic electrodes attached to said user, a minimum of at least one said galvanic electrode being attached to said user proximate to the mastoid bone behind each ear and a minimum of at least one said galvanic electrode attached to said user in a location proximate to the forehead area above each of said user's eyes.

9. An apparatus as claimed in claim 5, wherein said isolated current generator further comprises an output of direct current of approximately plus or minus one milliampere at an approximate band width of 2 Hz, and said direct current is adjustable such that said direct current may be altered in magnitude and band width to allow for the variable stimulation of said user.

10. An apparatus as claimed in claim 5, wherein said a three dimensional motion detection system comprising:

a. an electro-magnetic field generator whereby an electro-magnetic field is generated and is induced around said user;

b. a plurality of magnetic transmitters attached to said user and electrically connected to said electro-magnetic field generator whereby said plurality of magnetic transmitters sense the movement of said user and transmit output signals in response thereto.

* * * * *